US011534503B2

(12) United States Patent
Balaconis et al.

(10) Patent No.: US 11,534,503 B2
(45) Date of Patent: Dec. 27, 2022

(54) OXIDASE-BASED SENSORS AND METHODS OF USING

(71) Applicant: Profusa, Inc., Emeryville, CA (US)

(72) Inventors: Mary K. Balaconis, College Station, TX (US); Scott Nichols, College Station, TX (US)

(73) Assignee: Profusa, Inc., Emeryville, CA (US)

( * ) Notice: Subject to any disclaimer, the term of this patent is extended or adjusted under 35 U.S.C. 154(b) by 371 days.

(21) Appl. No.: 16/235,278

(22) Filed: Dec. 28, 2018

(65) Prior Publication Data
US 2020/0023079 A1 Jan. 23, 2020

Related U.S. Application Data

(60) Provisional application No. 62/611,151, filed on Dec. 28, 2017, provisional application No. 62/611,157, filed on Dec. 28, 2017.

(51) Int. Cl.
*A61K 49/00* (2006.01)
(52) U.S. Cl.
CPC ...... *A61K 49/0054* (2013.01); *A61K 49/0036* (2013.01); *A61K 49/0045* (2013.01)
(58) Field of Classification Search
CPC ............ A61K 49/0054; A61K 49/0036; A61K 49/0045
See application file for complete search history.

(56) References Cited

U.S. PATENT DOCUMENTS

| | | | |
|---|---|---|---|
| 5,220,036 A | 6/1993 | King | |
| 5,242,835 A | 9/1993 | Jensen | |
| 5,371,122 A | 12/1994 | Kawahara et al. | |
| 5,487,885 A | 1/1996 | Sovak et al. | |
| 5,837,865 A | 11/1998 | Vinogradov et al. | |
| 6,013,122 A | 1/2000 | Klitzman et al. | |
| 6,274,086 B1 | 8/2001 | Wlson et al. | |
| 6,362,175 B1 | 3/2002 | Vinogradov et al. | |
| 6,485,703 B1 | 11/2002 | Cote et al. | |
| 6,794,195 B2 | 9/2004 | Colvin, Jr. | |
| 7,060,503 B2 | 6/2006 | Colvin, Jr. | |
| 7,473,551 B2 | 1/2009 | Warthoe | |
| 7,939,332 B2 | 5/2011 | Colvin, Jr. | |
| 9,375,494 B2 | 6/2016 | Gamsey et al. | |
| 9,650,566 B2 | 5/2017 | Gamsey et al. | |
| 9,867,560 B2 | 1/2018 | Gamsey et al. | |
| 10,383,557 B2 | 8/2019 | Gamsey et al. | |
| 10,874,337 B2 | 12/2020 | Gamsey et al. | |
| 2004/0224021 A1* | 11/2004 | Omidian ................ A61L 27/56 424/484 |
| 2007/0110672 A1 | 5/2007 | Bellott et al. | |
| 2008/0075752 A1 | 3/2008 | Ratner et al. | |
| 2008/0311304 A1 | 12/2008 | Thompson et al. | |
| 2010/0303772 A1 | 12/2010 | McMillan et al. | |
| 2012/0165435 A1 | 6/2012 | Santhanam et al. | |
| 2012/0265034 A1 | 10/2012 | Wisniewski et al. | |
| 2013/0004785 A1 | 1/2013 | Carlson et al. | |
| 2013/0041200 A1 | 2/2013 | Sorokin et al. | |
| 2014/0286875 A1 | 9/2014 | Gamsey et al. | |
| 2016/0374601 A1 | 12/2016 | Gamsey et al. | |
| 2016/0376501 A1 | 12/2016 | Gamsey et al. | |
| 2018/0184956 A1 | 7/2018 | Gamsey et al. | |
| 2020/0008719 A1* | 1/2020 | Bremer ............... B01J 13/0052 |
| 2020/0107762 A1 | 4/2020 | Gamsey et al. | |
| 2021/0093239 A1 | 4/2021 | Gamsey et al. | |

FOREIGN PATENT DOCUMENTS

| | | |
|---|---|---|
| EP | 035261 | 1/1990 |
| WO | WO 2012/027593 | 3/2012 |
| WO | WO 2014/160258 | 10/2014 |

OTHER PUBLICATIONS

Musial et al. "Morphological patterns of poly(n-isopropylacrylamide) derivatives synthesized with EGDMA, DEGDMA, and TEGDMA crosslinkers for application as thermosensitive drug carriers", Chemical Papers 64 (6) 791-798 (2010) (Year: 2010).*
Alexeev et al., "High ionic strength glucose-sensing photonic crystal," Anal. Chem., 75:2316-2323 (2003).
Badylak et al., "Immune response to biologic scaffold materials," Seminars in Immunology, 20(2):109-116 (2008).
Borisov, S. M. et al., "Red light-excitable oxygen sensing materials based on platinum(II) and palladium(II) benzoporphyrins," Analytical Chemistry, 80(24):9435-9442 (Dec. 2008).
Braun et al., "Comparison of tumor and normal tissue oxygen tension measurements using oxylite or microelectrodes in rodents," Am. J. Physiol. Heart Circ. Physiol., 280(6):H2533-H2544 (2001).
Bridges et al., "Chronic inflammatory responses to microgel-based implant coatings," J Biomed. Mater. Res. A., 94(1):252-258 (2010).
Dunphy, I. et al., "Oxyphor R2 and G2: phosphors for measuring oxygen by oxygen-dependent quenching phosphorescence," Anal. Biochem., 310:191-198 (2002).
Hutter, L. H. et al., "Robust optical oxygen sensors based on polymer-bound NIR-emitting platinum(II)-benzoporphyrins," J. Mat. Chem. C., 36:7589-7598 (Jul. 2014).
Isenhath et al., "A mouse model to evaluate the interface between skin and a percutaneous device," J Biomed. Mater. Research, 83A:915-922 (2007).
Ju, Y. M. et al., "A novel porous collagen scaffold around an implantable biosensor for improving biocompatibility. I. In vitrol in vivo stability of the scaffold and in vitro sensitivity of the glucose sensor with scaffold," J Biomed. Mater. Research, 87A:136-146 (2008), Available online Dec. 17, 2007.
Kaehr et al., "Multiphoton fabrication of chemically responsive protein hydrogels for microactuation," PNAS USA, 105(26):8850-8854 (2008).
Kasprzak, S. E., "Small-scale polymer structures enabled by thiol-ene copolymer systems," Doctoral Dissertation, Georgia Institute of Technology, May 2009, 170 pages.

(Continued)

*Primary Examiner* — James W Rogers
(74) *Attorney, Agent, or Firm* — Cooley LLP

(57) ABSTRACT

Oxidase-based sensors and methods of using the sensors are provided.

12 Claims, 5 Drawing Sheets

(56) References Cited

OTHER PUBLICATIONS

Kloxin, A. M. et al., "Photodegradable hydrogels for dynamic tuning of physical and chemical properties," Science, 324:59-63 (2009).

Marshall et al., "Biomaterials with tightly controlled pore size that promote vascular in-growth," ACS Polymer Preprints, 45(2):100-101 (2004).

Menard et al., "Synthesis of tetraglucosyl- and tetrapolyamine-tetrabenzoporphyrin conjugates for an application in PDT," Bioorganic & Medicinal Chemistry, 17 (2009) 7647-7657, 11 pages.

Nielson, R. et al., "Microreplication and design of biological architectures using dynamicmask multiphoton lithography," Small, 5(1):120-125 (2009).

Ostendorf, A. et al., "Two-photon polymerization: a new approach to micromachining," Photonics Spectra, 40(10):72-79 (2006).

Ozdemir et al., "Axial pattern composite prefabrication of high-density porous polyethylene: experimental and clinical research," Plast. Reconstr. Surg., 115(1):183-196 (2005).

Phelps et al., "Bioartificial matrices fortherapeutic vascularization," PNAS USA, 107(8):3323-3328 (2010).

Quaranta, M. et al., "Indicators for optical oxygen sensors," Bioanalytical Reviews, 4(2-4):115-157 (Nov. 2012).

Rietveld, I. B. et al., "Dendrimers with tetrabenzoporphyrin cores: near infra-red phosphors for in vivo oxygen imaging," Tetrahedron, 59, 3821-3831, 2003.

Sanders et al., "Tissue response to single-polymer fibers of varying diameters: evaluation of fibrous encapsulation and macrophage density," J Biomed. Mater. Research, 52:231-237 (2000).

Sanders et al., "Tissue response to microfibers of different polymers: polyester, polyethylene, polylactic acid, and polyurethane," J Biomed. Mater. Research, 62(2):222-227 (2002).

Sanders et al., "Fibrous encapsulation of single polymer microfibers depends on their vertical dimension in subcutaneous tissue," J Biomed. Mater. Research, 67A:1181-1187 (2003).

Sanders et al., "Relative influence of polymer fiber diameter and surface charge on fibrous capsule thickness and vessel density for single-fiber implants," J Biomed. Mater. Research, 65A:462-467 (2003).

Sanders et al., "Polymer microfiber mechanical properties: a system for assessment and investigation of the link with fibrous capsule formation," J Biomed. Mater. Research, 67A:1412-1416 (2003).

Sanders et al., "Small fiber diameter fibro-porous meshes: tissue response sensitivity to fiber spacing," J Biomed Mater Research, 72A:335-342 (2005).

Sanders et al., "Fibro-porous meshes made from polyurethane micro-fibers: effects of surface charge on tissue response," Biomaterials, 26(7):813-818 (2005).

Tian et al., "Dually fluorescent sensing of PH and dissolved oxygen using a membrane made from polymerizable sensing monomers," Sensors and Actuators B, 147:714-722 (2010).

Tian et al., "Influence of matrices on oxygen sensing of three-sensing films with chemically conjugated platinum porphyrin probes and preliminary application for monitoring of oxygen consumption of *Escherichia coli* (*E. coli*)," Sensors and Actuators B, 150:579-587 (2010).

Tian, Y. et al., "A New Cross-linkable Oxygen Sensor Covalently Bonded into Poly(2-hydroxyethyl methacrylate)-co-Polyacrylamide Thin Film for Dissolved Oxygen Sensing," Chemistry Materials, 22(6):2069-2078 (2010).

Vinogradov, S. A. et al., "Pd tetrabenzoporphyrin-dendrimers: near-infrared phosphors for oxygen measurements by phosphorescense quenching," Proc. SPIE, 4626:193-200 (2002).

Wikipedia, "N,N'-Methylenebisacrylamide", Aug. 19, 2017 (Aug. 19, 2017), retrieved on Sep. 4, 2019 from https://en.wikipedia.org/w/index.php?title=N,N%27-Methylenebisacrylamide&oldid=796249249; entire document, 2 pages, especially p. 1 para 1.

International Search Report and Written Opinion for International Application No. PCT/US2018/067850, dated Sep. 24, 2019, 9 pages.

Extended European Search Report for European Application No. 20193383.5, dated Feb. 19, 2021, 13 pages.

\* cited by examiner

OXIDASE-BASED SENSORS AND METHODS OF USING

CROSS-REFERENCE TO RELATED APPLICATIONS

This application claims the benefit of U.S. Provisional Application Nos 62/611,151 filed Dec. 28, 2017, and 62/611,157 filed Dec. 28, 2017, the contents of which are hereby incorporated by reference in their entirety.

STATEMENT CONCERNING GOVERNMENT SUPPORT

This invention was made with government support under Grant No. W911NF-16-1-0341 awarded by the Defense Advanced Research Projects Agency and Grant No. R01EB016414 awarded by the National Institutes of Health. The government has certain rights in the invention.

FIELD OF THE INVENTION

The present disclosure is in the field of luminescent dyes, polymers and biosensors.

TECHNICAL BACKGROUND

In the management of many conditions, the regular measurement of analytes in vivo is required. For example, measurement of glucose in the blood is essential in order to ensure correct insulin dosing in diabetic patients. Furthermore, it has been demonstrated that in the long-term care of the diabetic patient, better control of the blood glucose levels can delay, if not prevent, the onset of retinopathy, circulatory problems, and other degenerative diseases often associated with diabetes. Thus there is a need for reliable and accurate self-monitoring of blood glucose levels by diabetic patients.

Currently, blood glucose is monitored by diabetic patients with the use of commercially available test strips or electrochemical biosensors (e.g. enzyme electrodes), both of which require the regular use of a lancet-type instrument to withdraw a suitable amount of blood each time a measurement is made. On average, the majority of diabetic patients would use such instruments to take a measurement of blood glucose twice a day. However, the US National Institutes of Health recently recommended that blood glucose testing should be carried out at least four times a day, a recommendation that has been endorsed by the American Diabetes Association. This increase in the frequency of blood glucose testing imposes a considerable burden on the diabetic patient, both in terms of financial cost and in terms of pain and discomfort, particularly in the long-term diabetic who has to make regular use of a lancet to draw blood from the fingertips. Thus, there is clearly a need for a better long-term glucose monitoring system that does not involve drawing blood from the patient.

The in vivo regular measurement of analytes, other than, or in addition to glucose, is important for a number of conditions. For example, lactate is a key biomarker for assessment of health, disease state, acute conditions (e.g. sepsis and trauma), metabolic activity, and exercise physiology. Increased blood lactate levels (hyperlactatemia) are common in critically ill patients, and often indicate issues such as inadequate tissue oxygenation, increased glycolysis, and organ failure, which tend to result in increased morbidity and mortality. Lactate is on the most frequently conducted standard analyte panels and is a standard diagnostic element in critical care. Measurements can be made in a central laboratory or using point-of care devices, but repeated blood draw measurements must be made throughout the treatment process. Additionally, these measurements are typically not started until the patient is admitted to the hospital. A lactate sensor that could be used in the field would allow first responders to begin monitoring immediately, providing an early assessment by the time the patient reaches the emergency room. Furthermore, such a sensor could be beneficial in non-traditional clinical environments such as developing countries and military field operations.

Over the last several decades, many attempts have been made to develop implanted sensors that provide frequent or continuous monitoring. For example, U.S. Pat. No. 4,703,756 to Gough et al. filed May 6, 1986, describes a sensor module for implantation in the body to monitor glucose and oxygen levels. However, due to electrical failure, degradation of the analyte recognition element (typically an enzyme), component degradation and delamination, these sensors typically fail after a relatively short period of time (e.g., hours to days). Another major failure mode of in vivo sensors is not failure of the sensor itself, but rather changes in the tissue immediately adjacent to the sensor due to the implantation of the sensor. The tissue at the interface of the sensor changes in such a way that it is no longer representative of the overall body state or disease state or analyte of interest.

U.S. Pat. No. 7,228,159 describes a sensor comprising a plurality of non-biodegradable sensing particles embedded in a biodegradable matrix for injection into the dermis. However, as the matrix degrades, the sensing particles are ingested by macrophages and removed from the implant site. Similarly, U.S. Pat. No. 6,671,527 describes a sensor which is injected into epidermis and is ejected over time due to the normal sloughing of skin. U.S. Patent Application No. 2009/0131773 describes a carbohydrate (e.g., glucose) sensor made up of at least two different variants of an appropriate competitive binding assay.

Nielsen et al. (2009) J. Diabetes Science and Technology 3(1):98-109, Billingsley et al. (2010) Anal. Chem. 82(9): 3707-3713 and McShane et al. (2000) IEEE Engineering in Medicine and Biology Magazine 19:36-45 describe implantation of analyte-sensing microspheres or nanospheres. These individual sensing particles are taken up by macrophages if they are too small, and can migrate through the tissue, which is not desirable for explantation and not desirable to have the fluorescent signal disperse in an uncontrolled way. If the sensing particles are too big to be taken up by macrophages, they undergo the typical foreign body response (FBR), which limits the proximity of capillaries with respect to the implant. As sensors become encapsulated by avascular tissue, they lose ability to accurately sense blood borne analytes and as they become engulfed by phagocytic cells (small particles), they lose contact with interstitial fluid, which is the compartment necessary to be sensed for components such as glucose. Therefore, current sensing technologies typically fail after only a short time in the body (e.g., 2-7 days for commercially available sensors).

Thus, there remains a clear need for sensing technologies that provide long-term (e.g., weeks, months or years) and accurate readings by remaining in contact with interstitial fluid (not the internal cellular environment) and remaining in close proximity to the vasculature so that the interstitial fluid surrounding the sensor is in constant rapid equilibrium with nearby capillaries.

SUMMARY OF THE INVENTION

In one embodiment, the invention is directed to a sensor for detecting an analyte, comprising one or more analyte sensing populations comprising: (a) one or more polymers, wherein the one or more polymers is formed from one or more methacrylate or acrylate monomers, one or more methacrylate or acrylate comonomers, and one or more methacrylate or acrylate crosslinkers; b) one or more oxidases; and c) one or more oxygen sensitive dyes. In certain embodiments, the analyte is lactate and the oxidase is lactate oxidase. In particular embodiments, the analyte is glucose and the oxidase is glucose oxidase. In yet other embodiments, the analyte is alcohol and the oxidase is alcohol oxidase.

In other embodiments, the monomer or comonomer is selected from the group consisting of: HEMA, BMAcrylate, HPMA, MMA, and nHA. In yet other embodiments, the comonomer is different from the monomer. In certain embodiments, the crosslinker is selected from the group consisting of: BPADA, EGDMA, HDDA, NPDA, PEA3, PEA4, PEGDA, TEGDMA and UDMA. In particular embodiments, the monomer is selected from the group consisting of: HEMA and HPMA, the comonomer is selected from the group consisting of: HPMA and nHA; and the crosslinker is selected from the group consisting of EGDMA.

In other embodiments, the sensor also comprises an oxygen reference population comprising an oxygen reference dye. In further embodiments, the oxygen reference population is between 0.1 mm and 5 mm from the one or more analyte sensing population.

In another embodiment, the invention is directed to a sensor for detecting an analyte, comprising one or more analyte sensing populations comprising: (a) one or more polymers, wherein the one or more polymers is formed from one or more acrylamide or methacrylamide monomers, one or more acrylamide or methacrylamide comonomers, and one or more acrylamide or methacrylamide crosslinkers; (b) one or more oxidases; and (c) an oxygen sensitive dye. In certain embodiments, the analyte is lactate and the oxidase is lactate oxidase. In particular embodiments, the analyte is glucose and the oxidase is glucose oxidase. In yet other embodiments, the analyte is alcohol and the oxidase is alcohol oxidase.

In yet other embodiments, the monomer or comonomer is selected from the group consisting of: dimethacrylamide, butylmethacrylamide, 2-hydroxypropylmethacrylamide, and N-(2-hydroxyethyl)methacrylamide. In still other embodiments, the crosslinker is selected from the group consisting of: methylenebisacrylamide, ethylenebisacrylamide, and polyethylene glycol diacrylamide.

In other embodiments, the sensor also comprises an oxygen reference population comprising an oxygen reference dye. In further embodiments, the oxygen reference population is between 0.1 mm and 5 mm from the one or more analyte sensing population.

In particular embodiments, the invention is also directed to a method for detecting an analyte in a subject, comprising placing a sensor as described herein in a subject, wherein the sensor generates detectable luminescent signal. In a further embodiment, the sensor generates detectable luminescent signal.

In yet other embodiments, the sensors described herein comprise an additional analyte sensing population. In a further embodiment, the additional analyte sensing population detects the analyte at a different oxygen concentration.

DETAILED DESCRIPTION

Oxidase-based sensors designed to measure analytes, such as lactate and glucose at physiological oxygen concentrations are described herein. Additionally, sensors containing distinct sensing populations measuring different concentration ranges are described.

Sensors described herein include one or more polymers, one or more oxidases, and one or more oxygen sensitive dyes. Exemplary oxidases include but are not limited to naturally occurring oxidases, genetically engineered oxidases, monooxygenases, glucose oxidase, lactate oxidase, pyruvate oxidase, alcohol oxidase, bilirubin oxidase, and histamine oxidase. Additionally, the oxidase-based sensors may further include one or more oxygen sensitive reference dye. As described herein, the measurement of the analyte by the described sensors does not require implanted electronics.

An embodiment relates to a sensor including two or more sensing populations. The two or more sensing populations may measure the same analyte, or the two or more sensing populations may measure different analytes. In an embodiment, one lactate sensing population measures lactate at a first percentage of oxygen, and a second sensing population measures lactate at a second percentage of oxygen. In a further aspect of the embodiment, additional sensing populations that measure lactate at different percentages of oxygen are also contemplated. Each sensing population includes one or more polymers, one or more lactate oxidases, and one or more oxygen sensitive dyes. This embodiment is non-limiting; although described for lactate, other oxidases, such as glucose oxidase, and their corresponding analytes are contemplated.

Measurement of an Analyte Using Oxidase-Based Sensors Described Herein

Figure 1A:
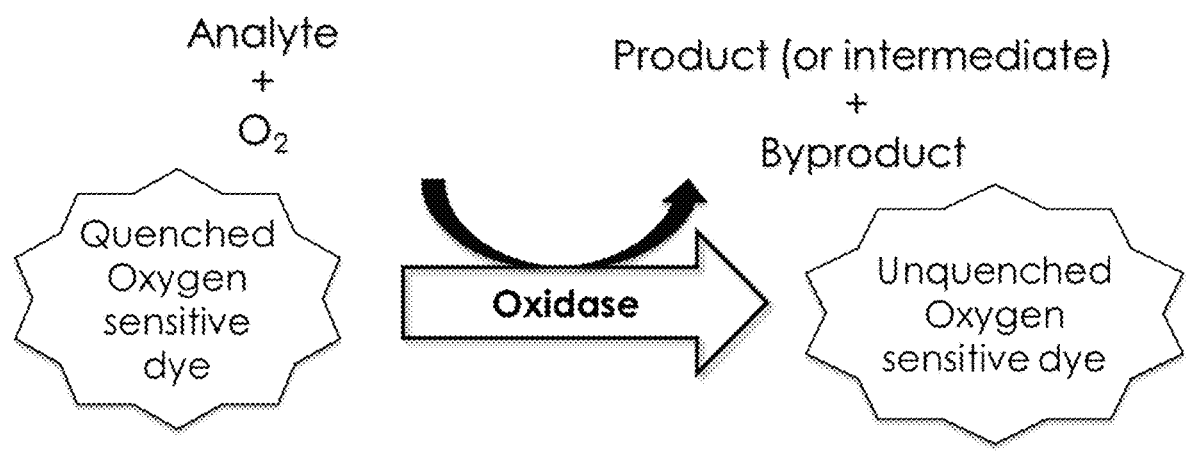
FIG. 1A shows a schematic of general sensing mechanism of the oxidase-based sensors described herein.
Figure 1B:
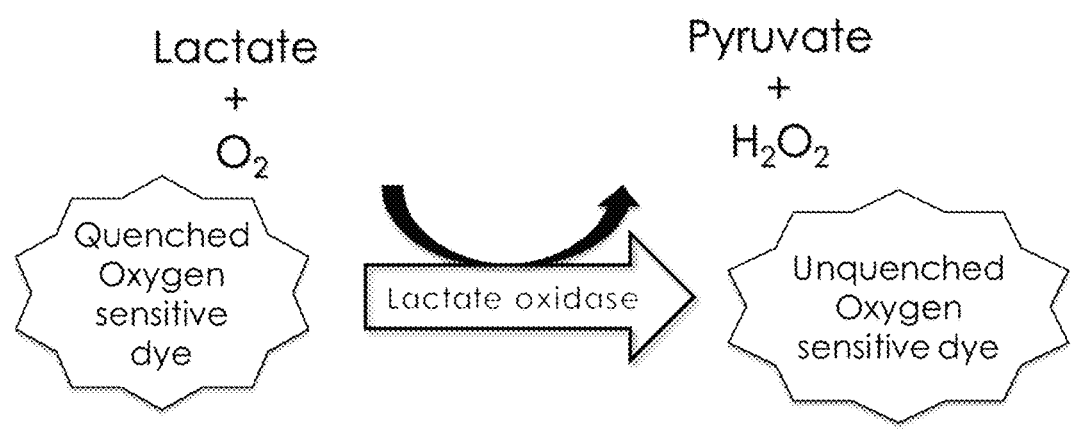
FIG. 1B shows a schematic of general sensing mechanism of the lactate oxidase-based sensors described herein.
Figure 1C:
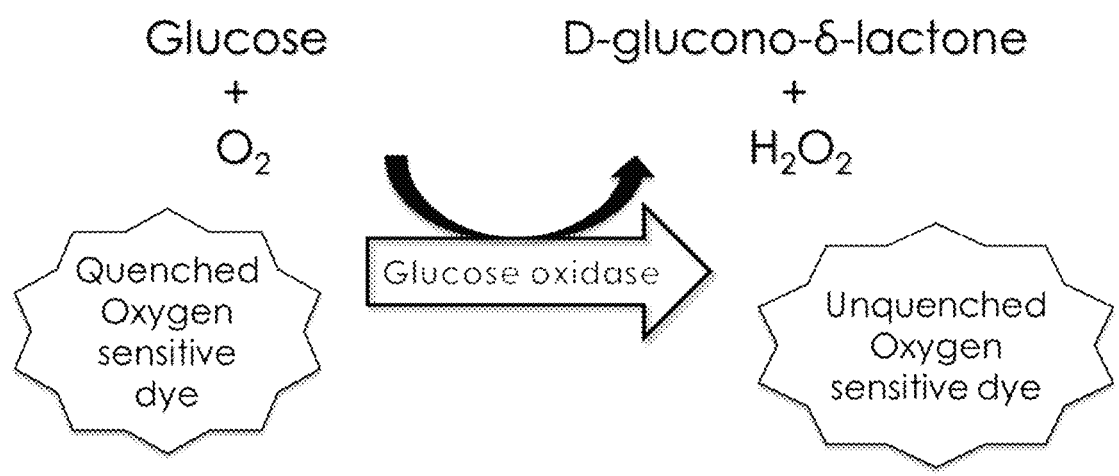
FIG. 1C shows a schematic of general sensing mechanism of the glucose oxidase-based sensors described herein.

Without being bound by a particular mechanism, it is believed that in the sensors described herein as the analyte is enzymatically converted, oxygen is consumed by the enzyme. The sensors measure the amount of oxygen, and the depletion of oxygen is directly related to the analyte concentration for a given oxygen concentration, that is, the concentration of oxygen and the analyte are inversely proportional. The particular analyte will be specific for the corresponding oxidase in the sensor; for example, lactate is the analyte for the lactate oxidase, and glucose is the analyte for the glucose oxidase. In an exemplary embodiment, without being bound by a particular mechanism, it is believed that in the exemplary sensors described herein, as the analyte is enzymatically converted, oxygen is consumed by the enzyme (FIG. 1A). The sensors measure the amount of oxygen, and the depletion of oxygen is directly related to the analyte concentration for a given oxygen concentration. In an exemplary embodiment, without being bound by a particular mechanism, it is believed that in the exemplary lactate sensors described herein, as the lactate is enzymatically converted, oxygen is consumed by the enzyme (FIG. 1B). The sensors measure the amount of oxygen, and the depletion of oxygen is directly related to the lactate concentration for a given oxygen concentration. In an exemplary embodiment, without being bound by a particular mechanism, it is believed that in the exemplary glucose sensors described herein, as the glucose is enzymatically converted, oxygen is consumed by the enzyme (FIG. 1C). The sensors measure the amount of oxygen, and the depletion of oxygen is directly related to the glucose concentration for a given oxygen concentration.

After initial sensor injection, measurements are collected non-invasively through luminescent near infrared (NIR) signals with a specially designed optical reader. In an embodiment, the optical reader is located outside of the body. These continuous analyte sensors have the potential to transform the field of analyte monitoring, such as lactate and glucose monitoring, by providing non-invasive, real-time, continuous analyte measurements in a user-friendly, cost-effective format.

Polymers

Sensors described herein may comprise several types of polymers. Each sensing population comprises one or more polymers, as described below. In addition, the sensors may further comprise one or more additional scaffold polymers. The scaffold polymers may form the scaffold of the sensor. The one or more sensing populations may be included in the scaffold. The one or more sensing populations may be covalently or non-covalently bound to the scaffold.

Polymers Useful in Oxidase-Based Sensors Functioning at a First Concentration of Oxygen In an aspect, oxidase-based sensors may be useful in detecting a particular analyte at a first concentration of oxygen. The first concentration of oxygen may be a concentration of oxygen that is found in the tissue under normal conditions. The first concentration of oxygen may be about 6% or less, about 5% or less, about 3% or less, about 2% or less, or about 1% or less.

Figure 2:
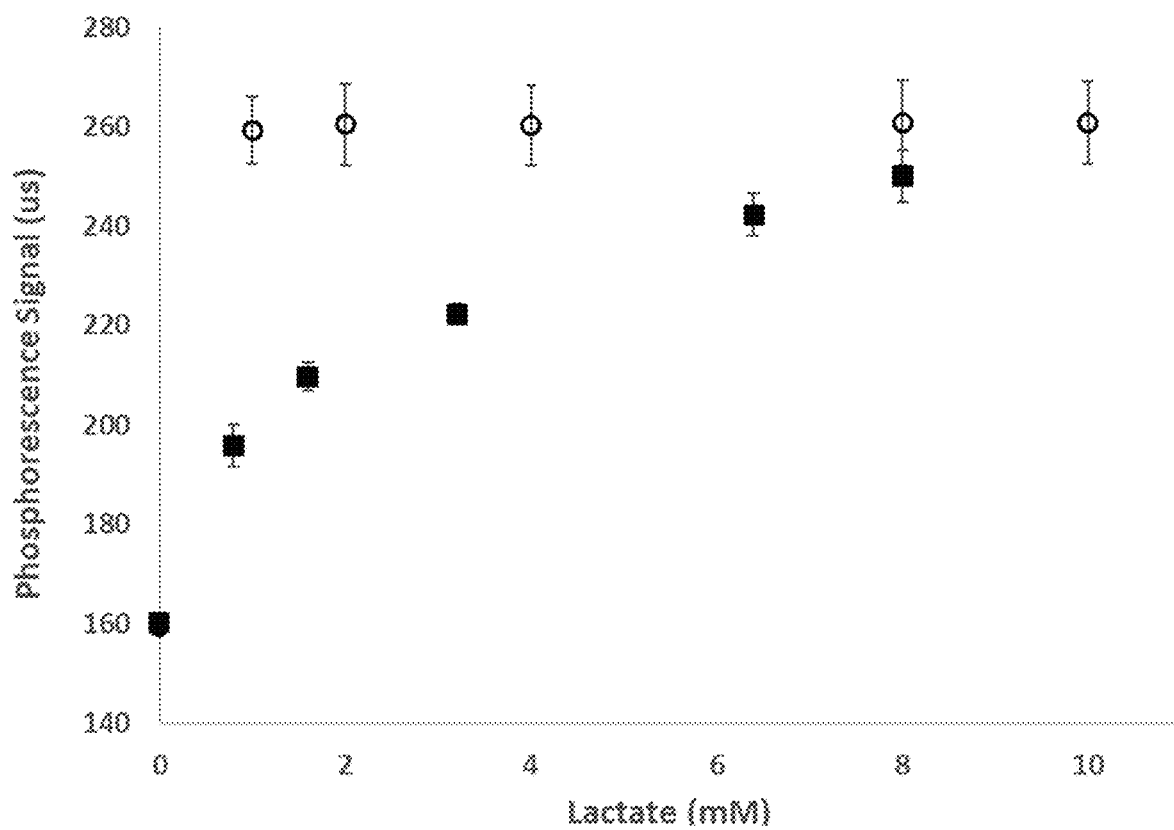
FIG. 2 illustrates the phosphorescence signal vs. lactate concentration of sensors including methacrylate monomers, acrylate comonomers, and methacrylate crosslinkers (closed squares) as compared to that of sensors including mixed methacrylate and methacrylamide monomers, comonomers, and crosslinkers (open circles). These measurements were taken at 2% oxygen.

In an exemplary embodiment, FIG. 2 illustrates the phosphorescence signal vs. lactate concentration of sensors including methacrylate monomers, acrylate comonomers, and methacrylate crosslinkers (closed squares) as compared to that of sensors including mixed methacrylate and methacrylamide monomers, comonomers, and crosslinkers (open circles). These measurements were taken at 2% oxygen. As shown, sensors including methacrylate monomers, acrylate comonomers, and methacrylate crosslinkers (closed squares) respond to increasing lactate in a manner that can be correlated to lactate concentration (at 2% oxygen). Sensors including mixed methacrylates and methacrylamides monomers, comonomers, and crosslinkers (open circles) did not show a correlation to the lactate concentrations tested (at 2% oxygen).

In an aspect, as illustrated in FIG. 2, the one or more polymers may be formed from one or more methacrylate or acrylate monomers, one or more methacrylate or acrylate comonomers, and one or more methacrylate or acrylate crosslinkers.

In an embodiment, the methacrylate or acrylate monomers and comonomers may be selected from the group consisting of: 3-chloro-2-hydroxypropyl methacrylate (3C2HPMA), 2-hydroxyethylmethacrylate (HEMA), pentafluorobenzyl methacrylate (PFBMA), butylmethacrylate (BMAcrylate), hydroxypropyl methacrylate (HPMA), methyl methacrylate (MMA), n-hexylacrylate (nHA), 2-methacryloyloxyethyl phosphorylcholine (MPC), hexyl methacrylate (HexMA), 2,2,3,3,4,4,4-heptafluorobutyl methacrylate (HFMA), and polyethylene glycol methacrylate (Mn=500) (PEGMA 500). In an embodiment, the monomer and the comonomer are not the same. In an aspect, the methacrylate or acrylate monomers and comonomers may be selected from the group consisting of: HEMA, HPMA, and nHA. In an aspect, the methacrylate or acrylate monomers and comonomers may be selected from the group consisting of: HPMA and nHA.

In an embodiment, the methacrylate or acrylate crosslinker may be selected from the group consisting of: bisphenol A glycerolate diacrylate (BPADA), ethylene glycol dimethacrylate (EGDMA), 1,6-hexanediol diacrylate (HDDA), neopentyl glycol diacrylate (NPDA), pentaerythritol triacrylate (PEA3), pentaerythritol tetraacrylate (PEA4), poly(etheylene glycol) diacrylate (Mn=700) (PEGDA 700), diurethane dimethacrylate (UDMA), di(trimethylolpropane) tetra-acrylate (DTMPTA) and tetraethylene glycol dimethacrylate (TEGDMA). In an embodiment, the crosslinker may be selected from the group consisting of: bisphenol A glycerolate diacrylate (BPADA), ethylene glycol dimethacrylate (EGDMA), 1,6-hexanediol diacrylate (HDDA), neopentyl glycol diacrylate (NPDA), pentaerythritol triacrylate (PEA3), pentaerythritol tetraacrylate (PEA4), poly(etheylene glycol) diacrylate (Mn=700) (PEGDA 700), and diurethane dimethacrylate (UDMA). In an aspect, the methacrylate or acrylate crosslinkers may be EGDMA.

In one embodiment, the one or more polymers may be formed from one or more methacrylamide or acrylamide monomers, one or more methacrylamide or acrylamide comonomers, and one or more methacrylamide or acrylamide crosslinkers. In an embodiment, the methacrylamide or acrylamide monomers, comonomers, and crosslinkers may be selected from the group consisting of: poly(ethylene glycol) diacrylamide (Mn=3700) (PEGDAAm (3700)), N-Isopropylacrylamide (NIPAAm), N-(2-hydroxyethyl) methacrylamide (HEMAM), dimethacrylamide (DMA), and N,N'-methylenebis(acrylamide) (Bis). In an aspect, the methacrylamide or acrylamide monomer or comonomer may be DMA.

The polymers of the present invention may be described by the weight percentage of up to three primary components (monomer, comonomer, and crosslinker) in the precursor solution. Prior to polymerization, these components may comprise about 10-90% volume of the precursor solution. In one embodiment, these components may comprise about 30-80% volume of the precursor solution. In one embodiment, these components may comprise about 50-70% volume of the precursor solution. In one embodiment, these components may comprise about 70% volume of the precursor solution. The remaining volumetric components may be sensing elements, dyes, co-solvents, crosslinkers that incorporate into the polymer.

The polymers of the present invention may be described by the weight percentage of up to three primary components (monomer, comonomer, and crosslinker) in the precursor solution.

Prior to polymerization, these components may comprise about 10-90% w/w of the precursor solution. In one embodiment, these components may comprise about 30-80% w/w of the precursor solution. In one embodiment, these components may comprise about 50-70% w/w of the precursor solution. In one embodiment, these components may comprise about 70% w/w of the precursor solution. The remaining volumetric components may be sensing elements, dyes, co-solvents, crosslinkers that incorporate into the polymer.

In particular embodiments, the weight percentage of methacrylate or acrylate monomer as compared to the other primary comonomers and crosslinkers in the precursor solution (Table 2) may be: about 40 to 100% w/w. In an embodiment, weight percentage of methacrylate or acrylate monomer (Table 2) may be: about 60 to 80% w/w. In an embodiment, weight percentage of methacrylate or acrylate monomer (Table 2) may be: about 60 to 75% w/w.

In particular embodiments, the weight percentage of methacrylate or acrylate comonomer as compared to the other primary monomers and crosslinkers in the precursor solution (Table 2) may be: 0 to 50% w/w. In an embodiment, weight percentage of methacrylate or acrylate comonomer (Table 2) may be: 5 to 30% w/w. In an embodiment, weight percentage of methacrylate or acrylate comonomer (Table 2) may be: 15 to 30% w/w.

In particular embodiments, the weight percentage of methacrylate or acrylate crosslinker as compared to the other primary monomers and comonomers in the precursor solution (Table 2) may be: 0 to 25% w/w. In an embodiment, weight percentage of methacrylate or acrylate crosslinker (Table 2) may be: 4 to 20% w/w. In an embodiment, weight percentage of methacrylate or acrylate crosslinker (Table 2) may be: 5 to 17% w/w.

In particular embodiments, the weight percentage of methacrylamide or acrylamide monomer as compared to the other primary comonomers and crosslinkers in the precursor solution (Table 3) may be: 85 to 100% w/w. In an embodiment, weight percentage of methacrylamide or acrylamide monomer (Table 3) may be: 85 to 95% w/w. In an embodiment, weight percentage of methacrylamide or acrylamide monomer (Table 3) may be: 90 to 95% w/w.

In particular embodiments, the weight percentage of methacrylamide or acrylamide crosslinker as compared to the other primary monomers and comonomers in the precursor solution (Table 3) may be: 0 to 15% w/w. In an embodiment, weight percentage of methacrylamide or acrylamide crosslinker (Table 3) may be: 4 to 12% w/w. In an embodiment, weight percentage of methacrylamide or acrylamide crosslinker (Table 3) may be: 5 to 10% w/w.

Analyte Sensing Protein

The sensor includes an analyte sensing protein. In an embodiment, the analyte sensing protein may be an oxidase. In an aspect, analyte sensing proteins may include but are not limited to naturally occurring oxidases, genetically engineered oxidases, monooxygenases, glucose oxidase, lactate oxidase, pyruvate oxidase, alcohol oxidase, bilirubin oxidase, and histamine oxidase.

Exemplary lactate oxidases include, but are not limited to, lactate 2-monooxygenase and lactate monooxygenase. Lactate 2-monooxygenase may be derived from different species including, but not limited to, *Aerococcus viridans*, *Pediococcus* species, and native microorganism. Glucose oxidase, also known as GOx or notatin, may be derived from different species including, but not limited to, *Penicillium notatum*, and *Aspergillus niger*. As shown in FIG. 1B, lactate oxidases consume oxygen and convert lactate to either pyruvate and hydrogen peroxide or acetate, carbon dioxide, and water. Similarly, glucose oxidases consume oxygen and convert glucose to hydrogen peroxide and D-glucono-δ-lactone. The reduction of oxygen in the vicinity of the enzyme can be measured by using an oxygen-sensitive dye, such as a porphyrin dye. These dye molecules are quenched in the presence of oxygen, so the reduction of oxygen by the action of oxidases causes an increase in luminescence and phosphorescent lifetime. Luminescence and phosphorescent lifetimes from the oxygen-sensitive dyes is thus proportional to the concentration of the analyte in the sensor.

In an embodiment, the one or more oxidases may be commercially available or produced by a user. The oxidase may be naturally occurring, may be recombinant, may contain mutations, or may have post transcriptional modifications such as glycosylation, or the like.

In an embodiment, the oxidase may be a monomer, dimer, trimer, or tetramer.

The lactate oxidase can be engineered from different species that include but are not limited to *Aerococcus viridans* and *Pediococcus* species. The glucose oxidase can be engineered from different species that include but are not limited to *Penicillium notatum*, and *Aspergillus niger*.

In an embodiment, the oxidase may be physically entrapped or chemically bound within the sensor. In an embodiment, the oxidase may be attached to the polymer, such through a covalent or non-covalent linkage. In an embodiment, the oxidase may not be chemically conjugated to the polymer. In another embodiment, the oxidase may be attached to the surface of the sensor, such as via covalent or non-covalent linkages. In yet another embodiment, oxidase may be present within the sensor through more than one of the above means, e.g., oxidase may be attached to the polymer via a covalent linkage and physically entrapped within the sensor. In an embodiment, the oxidase may be on the surface of the sensor and also within the sensor. In an embodiment, the sensor may be covered by an exterior coating.

Oxygen Sensitive Dye

Sensors described herein also include an oxygen sensitive dye. In an embodiment, the oxygen sensitive dye may be a porphyrin dye. The oxygen sensitive dye may be a NIR porphyrin molecule.

In an embodiment, the oxidase and the oxygen sensitive dye are co-located in the sensor.

In an embodiment, the oxygen sensitive dye may be selected from one described in U.S. Pat. No. 9,375,494, which is hereby incorporated by reference herein.

In an embodiment, the oxygen sensitive dye may be covalently attached to the polymer. In an embodiment, the oxygen sensitive dye may be covalently attached to the oxidase. In an embodiment, the oxygen sensitive dye may be non-covalently bound to the polymer.

Sensor Design

In an embodiment, the sensor may be 1-10 mm in length. The sensor may be 0.25-1 mm in diameter. In an embodiment, the sensor may be rod-shaped, spherical, block-like, cube-like, disk-shaped, cylindrical, oval, round, random or non-random configurations of fibers and the like. In an embodiment, the sensor may be a microsphere or a nanosphere.

In an embodiment, one sensor may include two or more sensing populations. These two or more sensing populations may be in distinct portions of the sensor. In an aspect, each of the two or more sensing populations may detect different analytes. In an aspect, each of the two or more sensing populations may detect different concentrations of the same analyte. In an aspect, a first sensing population of a sensor may measure an analyte at a first concentration of oxygen, and a second sensing population of the sensor may measure the analyte at a second concentration of oxygen. In an embodiment, the second concentration of oxygen may be higher than the first concentration of oxygen. In an embodiment, at least one of the concentrations of oxygen may be a physiological concentration of oxygen.

In an embodiment, one or more of the sensing populations may be microspheres, nanospheres, microparticles, nanoparticles, and the like. In an embodiment, the scaffold of the sensor may include a polymer that be different from, or the same as, the polymer in a sensing population.

In an embodiment, the sensor may include distinct layers where the oxidase is physically entrapped or chemically bound to or within specific layers of the sensor. In a further embodiment, the sensor may include additional layers; the additional layers may provide other features such as mechanical strength, elasticity, conductivity or other properties. The additional layers may detect different analytes or different concentrations of the same analyte. The additional layers may include a reference dye.

In certain embodiments, the sensor includes additional moieties (e.g., non-sensing or additional sensing moieties different from the sensing moieties), for example reference (or calibration) moieties. Reference or calibration moieties include, but are not limited to, dyes, fluorescent particles, lanthanides, nanoparticles, microspheres, quantum dots or other additives or elements of the implant whose signal does not change due to the presences of the analyte (e.g., glucose). See, e.g., Chaudhary et al. (2009) Biotechnology and Bioengineering 104(6):1075-1085, which is hereby incorporated herein by reference in its entirety. Fluctuations in the reference (calibration) signal(s) can be used to correct or calibrate the sensing signal(s).

Oxygen Reference Dye

In an embodiment, the oxidase-based sensor may also include an additional oxygen-sensitive dye that serves as a reference for the amount of locally present oxygen.

In an embodiment, the oxygen reference dye may be a porphyrin dye. The oxygen reference dye may be a NIR porphyrin ring molecule. In an embodiment, the oxygen reference dye may include the same type of chemistry as the oxygen-sensitive dye. The oxygen reference dye may be selected from one described in U.S. Pat. No. 9,375,494, which is hereby incorporated by reference herein.

The oxygen reference dye may be covalently or non-covalently attached to a polymer. The polymer and the one or more oxygen reference dyes may form an oxygen reference population. The polymer of the oxygen reference population may be the same or different from the polymer of the scaffold. In an embodiment, one or more of the oxygen reference dye populations may be microspheres, nanospheres, microparticles, nanoparticles, and the like.

In an embodiment, the one or more analyte sensing populations is adjacent to the oxygen reference population with no space between. In an embodiment, there may be a spacer between the analyte sensing portion and the oxygen reference population. The spacer may include the same or different polymer materials as the analyte and oxygen sensing populations. In an aspect, the spacer may separate the analyte sensing populations and oxygen reference population between 0.1 and 5 mm. In an embodiment, the spacer may be between 0.5 and 2 mm. In an embodiment, the spacer may be greater than 0.2 mm. In an embodiment, the spacer may be greater than 0.5 mm.

In an embodiment, multiple sensors containing the same or different sensing populations may be implanted near each other. For example, one or more sensors containing only the first sensing population may be implanted near one or more sensors containing only the second sensing population. For example, one or more sensors containing only the oxygen reference population may be implanted near the one or more sensors containing only the first sensing population and/or the second sensing population. In an aspect, one sensor may include multiple sensing populations. For example, one or more sensors containing the first sensing population and the second sensing population may be implanted near one or more sensors containing a third sensing population. For example, one or more sensors containing both the first sensing population and the second sensing population may be implanted near one or more sensors containing one or more oxygen reference populations. In an aspect, a sensor may include one or more sensing populations and one or more reference populations. The sensors may be implanted in a particular design, such as a ring, or another geometry.

Properties

In addition, the scaffold of the invention may be constructed such that it has conduits, pores or pockets that are hollow or filled with degradable, angiogenic, or other substances (e.g. stem cells). Once in the body, the biodegradation of the material filling the conduits, pores or pockets, creates space for tissue, including capillaries to integrate with the material. The degradable material that initially fills the conduits, pores or pockets may enhance vessel growth or tissue growth within the scaffold. This architecture promotes new vessel formation and maintains healthy viable tissue within and around the implant.

Methods of Using Oxidase-Based Sensors

Oxidase-based sensors as described herein are useful in the monitoring of a number of conditions. The oxidase-based sensors may be placed subcutaneously, surrounding tissue of muscle, subcutaneous fat, dermis, in muscle, in skin, in the limbs, sternum, neck, ear, brain, or other locations.

In an embodiment, the lactate sensors described herein may be useful in monitoring trauma, sepsis, exercise physiology/performance optimization, skin grafts, wound healing, shock, and other disease states as described in Andersen et al. (2013) Mayo Clin Proc 88 (10): 1127-1140, which is hereby incorporated herein by reference in its entirety.

EXAMPLES

Example 1

Lactate Sensor

Figure 4:
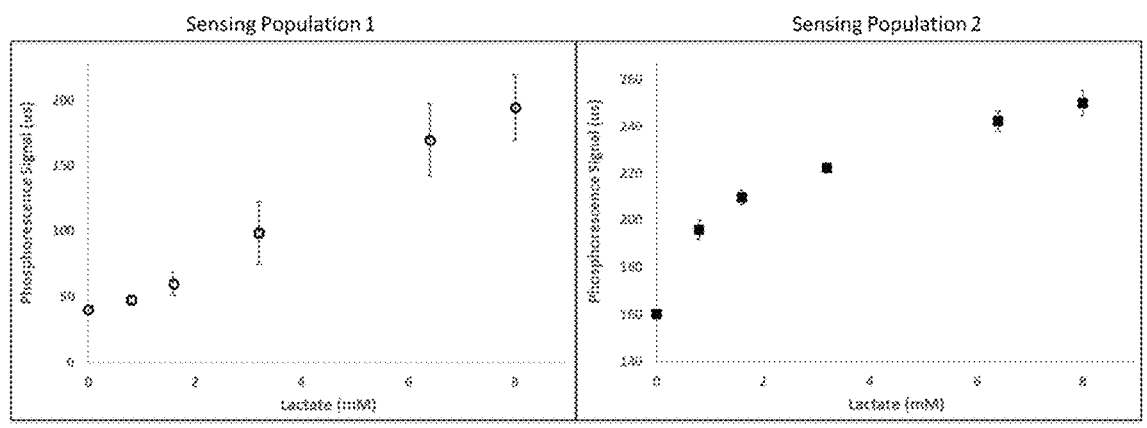
FIG. 4 shows the performance of lactate sensors with sensing population 1 at 21% oxygen and sensing population 2 at 2% oxygen. Sensing population 1 includes mixed methacrylate and methacrylamide monomers, comonomers, and crosslinkers. Sensing population 2 includes methacrylate monomers, acrylate comonomers, and methacrylate crosslinkers.

Sensor Fabrication: Formulations with monomer mixtures for each sensor type are listed in Table 1 and apply to FIGS. 2 and 4. FIG. 2 contains formulations 2 (open circles) and 3 (closed squares). FIG. 4 contains formulations 1 (open circles) and 3 (closed squares). All formulations contained 0.56 mM 2-aminoethylmethacrylate in distilled water, 19 mM of Irgacure 651, and enzymatic components were dissolved in 20 mM PBS such that the PBS volume was 18% of the total mixture volume. The mixture was then polymerized. After polymerization, the polymeric material was rinsed with distilled water and placed in 20 ml of PBS with 0.7 mM N-(3-dimethylaminopropyl)-N'-ethylcarbodiimide hydrochloride (EDC) and 1.8 mM N-hydroxysulfosuccinimide (NHS) for at least 8 hours except for Formulation 2. The material was then removed, rinsed three times with PBS, and cut into sensor rods with dimensions of 5 mm×0.5 mm×0.5 mm.

Sensor Performance Testing: Sensors were placed in a customized test fixture with controllable oxygen levels. All sensors were tested in either 500 or 800 ml of PBS and allowed to equilibrate to either 2 or 21% oxygen at 37° C. Pumps were used to dispense lactate at stepwise increases in concentration (Table 1). At each lactate concentration, the sensor phosphorescence signal was equilibrated. Response curves were generated by averaging the phosphorescence signal of the last 2 minutes of each step prior to increasing lactate.

TABLE 1

Lactate sensor formulations depicted in FIGS. 2 and 4.

| Formulation | Total Volume (uL) | Monomer/ Comonomer/ Crosslinker | Monomer/ Comonomer/ Crosslinker (M) | Cosolvents | Dye | Enzymatic Components (w/v %) | Oxygen Conc. (%) | Lactate Conc. (mM) |
|---|---|---|---|---|---|---|---|---|
| 1 | 500 | HEMA/ DMA/ EGDMA | 3.0/ 0.9/ 0.3 | 1.4M DMSO[1] 2.9M EG[2] | 1 mM BMAP[3] in DMSO | 2.1% LOx[4] 0.3% catalase[5] | 21 | 0, 0.8, 1.6, 3.2, 6.4, 8 |
| 2 | 500 | HEMA/ DMA/ EGDMA | 3.0/ 0.9/ 0.3 | 3.7M DMSO | 1 mM BMAP in DMSO | 2.1% LOx[6] | 2 | 0, 1, 2, 4, 8, 10 |
| 3 | 125 | HEMA/ nHA/ EGDMA | 2.6/ 0.8/ 0.3 | 2.7M NMP | 1 mM BMAP in NMP | 2.1% LOx[7] 0.3% catalase[8] | 2 | 0, 0.8, 1.6, 3.2, 6.4, 8 |

[1]Dimethysulfoxide
[2]Ethylene glycol
[3]Pd-BMAP-AEME-4 (U.S. Pat. No. 9,375,494)
[4]from *Aerococcus viridans*
[5]from bovine liver
[6]from *Aerococcus viridans*
[7]from *Aerococcus viridans*
[8]from bovine liver Example 2

Lactate Sensors

TABLE 2

Methacrylate and acrylate-based oxidase-based sensor compositions (w/w % of monomer and/or polymer content of major components)

| Monomer | Comonomer | Crosslinker | Wt % Monomer | Wt % Comonomer | Wt % Crosslinker |
|---|---|---|---|---|---|
| 3-chloro-2-hydroxypropyl methacrylate | | tetraethylene glycol dimethacrylate | 98.2 | | 1.8 |
| 2-hydroxyethyl methacrylate | | tetraethylene glycol dimethacrylate | 98 | | 2 |
| 2-hydroxyethyl methacrylate | | ethylene glycol dimethacrylate | 95.1 | | 4.9 |
| hydroxypropyl methacrylate | | ethylene glycol dimethacrylate | 95 | | 5 |
| 2-hydroxyethyl methacrylate | | pentaerythritol tetraacrylate | 94.4 | | 5.6 |
| 2-hydroxyethyl methacrylate | | pentaerythritol triacrylate | 94.4 | | 5.6 |
| pentafluorobenzyl methacrylate | | ethylene glycol dimethacrylate | 92.3 | | 7.7 |
| 2-hydroxyethyl methacrylate | | 1,6-hexanediol diacrylate | 92.1 | | 7.9 |
| 2-hydroxyethyl methacrylate | | ethylene glycol dimethacrylate | 90.2 | | 9.8 |
| hydroxypropyl methacrylate | | ethylene glycol dimethacrylate | 90 | | 10 |
| 2-hydroxyethyl methacrylate | | diurethane dimethacrylate | 89.8 | | 10.2 |
| 2-hydroxyethyl methacrylate | | di(trimethylolpropane) tetra-acrylate | 89.6 | | 10.4 |
| 2-hydroxyethyl methacrylate | | pentaerythritol triacrylate | 88.9 | | 11.1 |
| hydroxypropyl methacrylate | | pentaerythritol triacrylate | 88.7 | | 11.3 |

TABLE 2-continued

Methacrylate and acrylate-based oxidase-based sensor compositions
(w/w % of monomer and/or polymer content of major components)

| Monomer | Comonomer | Crosslinker | Wt % Monomer | Wt % Comonomer | Wt % Crosslinker |
|---|---|---|---|---|---|
| 2-hydroxyethyl methacrylate | | diurethane dimethacrylate | 79.6 | | 20.4 |
| 2-hydroxyethyl methacrylate | 2-methacryloyloxyethyl phosphorylcholine | ethylene glycol dimethacrylate | 87.6 | 0.5 | 11.9 |
| 2-hydroxyethyl methacrylate | hydroxypropyl methacrylate | ethylene glycol dimethacrylate | 85.7 | 9.4 | 4.9 |
| 2-hydroxyethyl methacrylate | hexyl methacrylate | ethylene glycol dimethacrylate | 82.6 | 7.4 | 10 |
| 2-hydroxyethyl methacrylate | butylmethacrylate | ethylene glycol dimethacrylate | 82.3 | 7.7 | 10 |
| 2-hydroxyethyl methacrylate | methyl methacrylate | ethylene glycol dimethacrylate | 82 | 8 | 9.9 |
| 2-hydroxyethyl methacrylate | hydroxypropyl methacrylate | ethylene glycol dimethacrylate | 81.3 | 8.9 | 9.8 |
| 2-hydroxyethyl methacrylate | 2,2,3,3,4,4,4-heptafluorobutyl methacrylate | ethylene glycol dimethacrylate | 79.2 | 11.3 | 9.6 |
| 2-hydroxyethyl methacrylate | n-hexyl acrylate | ethylene glycol dimethacrylate | 78.7 | 16.3 | 5.1 |
| 2-hydroxyethyl methacrylate | n-hexyl acrylate | ethylene glycol dimethacrylate | 78.5 | 13 | 8.5 |
| 2-hydroxyethyl methacrylate | n-hexyl acrylate | ethylene glycol dimethacrylate | 78.5 | 11.5 | 10 |
| 2-hydroxyethyl methacrylate | butylmethacrylate | ethylene glycol dimethacrylate | 78.4 | 16.5 | 5.1 |
| 2-hydroxyethyl methacrylate | n-hexyl acrylate | ethylene glycol dimethacrylate | 77.9 | 7.2 | 15 |
| 2-hydroxyethyl methacrylate | hydroxypropyl methacrylate | ethylene glycol dimethacrylate | 76.8 | 8.4 | 14.8 |
| 2-hydroxyethyl methacrylate | hydroxypropyl methacrylate | ethylene glycol dimethacrylate | 76.3 | 18.8 | 4.9 |
| 2-hydroxyethyl methacrylate | hexyl methacrylate | ethylene glycol dimethacrylate | 74.8 | 15 | 10.2 |
| 2-hydroxyethyl methacrylate | n-hexyl acrylate | ethylene glycol dimethacrylate | 74.5 | 15.4 | 10.1 |
| 2-hydroxyethyl methacrylate | butylmethacrylate | ethylene glycol dimethacrylate | 74.3 | 15.6 | 10.1 |
| 2-hydroxyethyl methacrylate | methyl methacrylate | ethylene glycol dimethacrylate | 73.7 | 16.2 | 10 |
| 2-hydroxyethyl methacrylate | hydroxypropyl methacrylate | ethylene glycol dimethacrylate | 72.4 | 17.8 | 9.8 |
| 2-hydroxyethyl methacrylate | polyethylene glycol methacrylate (Mn = 500) | ethylene glycol dimethacrylate | 71.5 | 18.7 | 9.7 |
| 2-hydroxyethyl methacrylate | 3-chloro-2-hydroxypropyl methacrylate | ethylene glycol dimethacrylate | 70.5 | 19.9 | 9.6 |
| 2-hydroxyethyl methacrylate | n-hexyl acrylate | ethylene glycol dimethacrylate | 70 | 24.8 | 5.2 |
| 2-hydroxyethyl methacrylate | 2,2,3,3,4,4,4-heptafluorobutyl methacrylate | ethylene glycol dimethacrylate | 68.7 | 22 | 9.3 |
| hydroxypropyl methacrylate | 2-hydroxyethyl methacrylate | ethylene glycol dimethacrylate | 67.3 | 22.8 | 9.9 |
| 2-hydroxyethyl methacrylate | n-hexyl acrylate | ethylene glycol dimethacrylate | 66.2 | 23.5 | 10.3 |
| 2-hydroxyethyl methacrylate | n-hexyl acrylate | tetraethylene glycol dimethacrylate | 65.9 | 23.4 | 10.7 |
| 2-hydroxyethyl methacrylate | n-hexyl acrylate | poly(ethylene glycol) diacrylate (Mn = 700) | 65.6 | 23.3 | 11.1 |
| 2-hydroxyethyl methacrylate | methyl methacrylate | ethylene glycol dimethacrylate | 65.2 | 24.6 | 10.1 |
| 2-hydroxyethyl methacrylate | hydroxypropyl methacrylate | ethylene glycol dimethacrylate | 64 | 27 | 9 |
| 2-hydroxyethyl methacrylate | hydroxypropyl methacrylate | ethylene glycol dimethacrylate | 63.4 | 26.7 | 9.9 |
| 2-hydroxyethyl methacrylate | n-hexyl acrylate | poly(ethylene glycol) diacrylate (Mn = 700) | 61.6 | 21.9 | 16.5 |
| 2-hydroxyethyl methacrylate | n-hexyl acrylate | poly(ethylene glycol) diacrylate (Mn = 700) | 57.6 | 20.4 | 21.9 |
| 2-hydroxyethyl methacrylate | methyl methacrylate | ethylene glycol dimethacrylate | 47.6 | 42 | 10.4 |
| 2-hydroxyethyl methacrylate | hydroxypropyl methacrylate | ethylene glycol dimethacrylate | 45.4 | 44.7 | 9.9 |

TABLE 3

Methacrylamide and acrylamide-based oxidase-based sensor compositions (w/w % of monomer and/or polymer content of major components)

| Monomer | Crosslinker | Wt % Monomer | Wt % Crosslinker |
|---|---|---|---|
| poly(ethylene glycol) diacrylamide (Mn = 3700) | | 100 | |
| N-Isopropylacrylamide | N,N'-methylenebis(acrylamide) | 95.2 | 4.8 |
| N-(2-hydroxyethyl)methacrylamide | N,N'-methylenebis(acrylamide) | 88.9 | 11.1 |

Example 3

Glucose Sensors

Sensors of Table 4 were be fabricated as follows: 0.56 mM (3-aminopropyl)methacrylamide, 15 mM of 2,2'-azobis[2-(2-imidazolin-2-yl)propane]dihydrochloride, and enzymatic components were dissolved in 10 mM PBS such that the PBS volume was 21% of the total mixture volume. All components were mixed, molded, and polymerized. Glucose sensors were then placed in 20 ml of PBS with 0.7 mM N-(3-dimethylaminopropyl)-N'-ethylcarbodiimide hydrochloride (EDC) and 1.8 mM N-hydroxysulfosuccinimide (NHS) for at least 8 hours. Oxygen sensors were placed in 20 ml of PBS for at least 1 hour. After soaking in PBS, sensors were placed in distilled water for at least 15 minutes then removed and dried under vacuum. After drying, sensors were ethylene oxide sterilized for implantation.

TABLE 4

Figure 3:
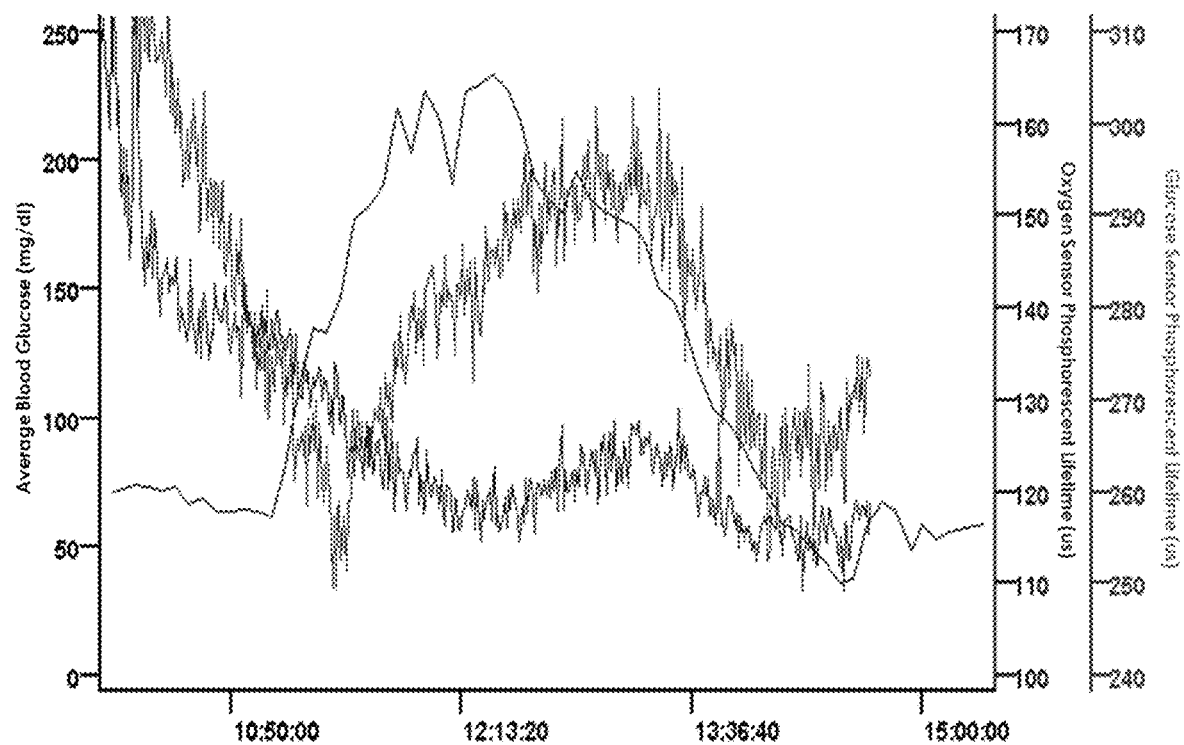
FIG. 3 shows the performance of the glucose oxidase containing sensor (red line) in pigs, as compared to glucose levels (black line) and oxygen levels (blue line).

Oxygen and glucose sensor formulations depicted in FIG. 3.

| Sensor | Total Volume (uL) | Monomer/ Comonomer/ Crosslinker | Monomer/ Comonomer/ Crosslinker (M) | Cosolvents | Dye | Enzymatic Components (w/v %) |
|---|---|---|---|---|---|---|
| Glucose Sensor | 125 | HEMA/ nHA/ EGDMA | 3.0/ 0.5/ 0.3 | 0.9M DMSO 3.2M EG | 1 mM BMAP in DMSO | 3.6% glucose oxidase[9]/0.6% catalase[10] |
| Oxygen Sensor | 125 | HEMA/ nHA/ EGDMA | 3.0/ 0.5/ 0.3 | 1.5 M DMSO 3.2M EG | 1 mM BMAP in DMSO | N/A |

Sensors were injected subcutaneously into a female Sinclair mini-pig with an 18 gauge needle attached to a custom built trocar-like injection device. Sensor signal was monitored throughout the experiment using a custom handheld optical reader system. Under anesthesia, a dextrose infusion was administered to the animal to achieve a glucose challenge. Blood glucose measurements were recorded using a commercially available handheld glucometer to track increases and decreases in blood glucose values. FIG. 3 shows the blood glucose measurements and phosphorescent lifetime signals of glucose and oxygen sensors implanted for 28 days (n=1 each).

Example 4

Alcohol Sensors

Figure 5:
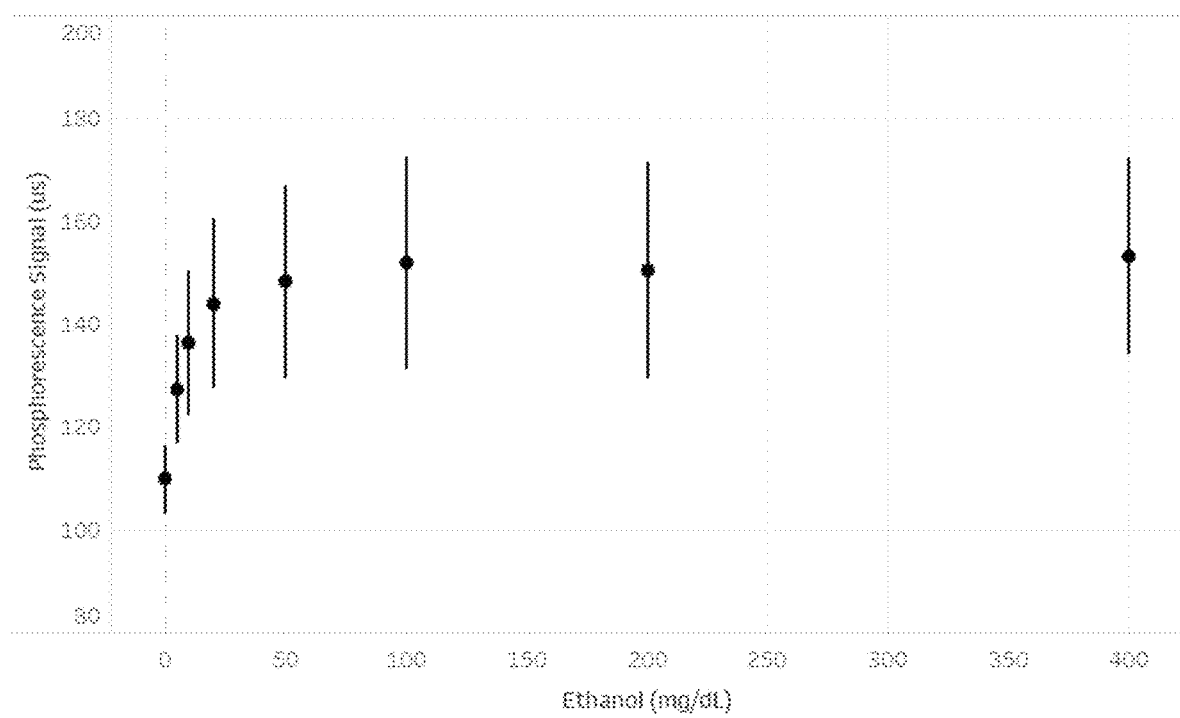
FIG. 5 illustrates alcohol oxidase-based sensors tested at 5% oxygen. Sensors show a response when exposed to increasing concentrations of ethanol.

Alcohol sensors were made by dissolving enzymatic components (e.g., alcohol oxidase) and 2,2-dimethoxy-1,2-diphenylethan-1-one into one or more solvents. This mixture was combined 1:1 (v/v) with a solution containing 90% HEMA and 10% ethylene glycol dimethacrylate (wt %). The mixture was then polymerized. After polymerization, the polymeric material was rinsed with distilled water and cut into sensor rods with dimensions of 5 mm×0.5 mm×0.5 mm and stored in PBS until tested. Sensor Performance Testing: Sensors were placed in a customized test fixture with controllable oxygen levels. All sensors were tested in either 500 or 800 mL of PBS and allowed to equilibrate to 5% oxygen at 37° C. Pumps were used to dispense ethanol at stepwise increases in concentration. At each ethanol concentration, the sensor phosphorescence signal was equilibrated. Response curves were generated by averaging the phosphorescence signal of the last 2 minutes of each step prior to increasing ethanol. An increase in sensor signal with increasing concentrations of ethanol exhibits a clear sensitivity to the analyte added to the test vessel. FIG. 5 illustrates alcohol oxidase-based sensors tested at 5% oxygen. Sensors show a response when exposed to increasing concentrations of ethanol.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A sensor for detecting an analyte, comprising one or more analyte sensing populations comprising:
   (a) one or more polymers, wherein the one or more polymers is formed from one or more monomers, one or more comonomers and one or more crosslinkers; wherein the one or more monomers are selected from the group consisting of: 2-hydroxyethyl methacrylate (HEMA) and hydroxypropyl methacrylate (HPMA); the one or more comonomers are selected from the group consisting of: HPMA and n-hexylacrylate (nHA); and the one or more crosslinkers is ethylene glycol dimethacrylate (EGDMA); wherein the one or more comonomers are is different from the one or more monomers;
   (b) one or more oxidases; and
   (c) one or more oxygen sensitive dyes.

2. The sensor of claim 1, wherein the analyte is lactate and the one or more oxidases is lactate oxidase.

3. The sensor of claim 1, wherein the analyte is glucose and the one or more oxidases is glucose oxidase.

4. The sensor of claim 1, further comprising an oxygen reference population comprising an oxygen reference dye.

5. A method for detecting an analyte in a subject, comprising placing a sensor of claim 1 in a subject, wherein the sensor generates detectable luminescent signal.

6. The sensor of claim 1, further comprising an additional analyte sensing population.

7. The sensor of claim 6, wherein the additional analyte sensing population detects the analyte at a different oxygen concentration.

8. The sensor of claim 4, wherein the oxygen reference population is between 0.1 mm and 5 mm from the one or more analyte sensing populations.

9. The sensor of claim 1, wherein the analyte is alcohol and the one or more oxidases is alcohol oxidase.

10. The sensor of claim 1 wherein the one or more polymers are formed from HEMA monomer, HPMA comonomer, and EGDMA crosslinker.

11. The sensor of claim 10, wherein:
    the HEMA monomer is 40 wt % to 80 wt % of the one or more polymers;
    the HPMA comonomer is 15 wt % to 30 wt % of the one or more polymers; and
    the EGDMA is 4 wt % to 20 wt % of the one or more polymers.

12. The sensor of claim 10, wherein:
    the HEMA monomer is about 63 wt % of the one or more polymers;
    the HPMA comonomer is about 27 wt % of the one or more polymers; and
    the EGDMA is about 10 wt % of the one or more polymers.

* * * * *